United States Patent [19]

Evans

[11] Patent Number: 5,219,726
[45] Date of Patent: Jun. 15, 1993

[54] PHYSICAL MAPPING OF COMPLEX GENOMES

[75] Inventor: Glen A. Evans, Encinitas, Calif.

[73] Assignee: The Salk Institute for Biological Studies, San Diego, Calif.

[21] Appl. No.: 360,254

[22] Filed: Jun. 2, 1989

[51] Int. Cl.⁵ .......................... C12Q 1/68; C12N 1/20; G01N 33/566; G01N 33/48

[52] U.S. Cl. .................................... 435/6; 435/252.3; 436/501; 436/94; 935/77; 935/78; 935/79; 935/80

[58] Field of Search .......................... 435/6, 91, 320.1; 536/26, 27, 28, 29; 935/77, 78

[56] References Cited

U.S. PATENT DOCUMENTS 4,766,072  8/1988  Jendrisak et al. .................... 435/91

OTHER PUBLICATIONS

Skolnick et al., Genomics 2(4): 273-279 (May 1988).
Olson et al., Proc. Natl. Acad. Sci. USA 83, 7826 (1986).
Coulson et al., Proc. Natl. Acad. Sci. USA 83, 7821.
Kohara et al., Cell 50, 495 (1987).
Lander et al., Genomics 2, 231 (1988).
Wahl et al., Proc. Natl. Acad. Sci. USA 84, 2160 (1987).
Evans et al., Methods in Enzymology 152, 604 (1987).
DiLella et al., Methods in Enzymology 152, 199 (1987).
Bates et al., Gene 26, 137 (1983).
Ehrich et al., Gene 57, 229 (1987).
Pirrotta et al., The EMBO Journal 2, 927 (1983).
Poustka et al., Cold Springs Harbor Symposia on Quantitative Biology LI, 131 (1986).
Evans et al., Immunogenetics 28, 365 (1988).

Primary Examiner—Amelia Burgess Yarbrough
Assistant Examiner—Stephanie W. Zitomer
Attorney, Agent, or Firm—Fitch, Even, Tabin & Flannery

[57] ABSTRACT

Method for simultaneous identification of overlapping cosmid clones among multiple cosmid clones and the use of the method for mapping complex genomes are provided. A library of cosmid clones that contains the DNA to be mapped is constructed and arranged in a manner such that individual clones can be identified and replicas of the arranged clones prepared.

In preferred embodiments, the clones are arranged in a two dimensional matrix. In such embodiments, the cosmid clones in a row are pooled, mixed probes complementary to the ends of the DNA inserts int he pooled clones are synthesized, hybridized to a first replica of the library. Hybridizing clones, which include the pooled row, are identified. A second portion of clones is prepared by pooling cosmid clones that correspond to a column in the matrix. The second pool thereby includes one clone from the first portion pooled clones. This common clone is located on the replica at the intersection of the column and row. Mixed probes complementary to the ends of the DNA inserts in the second pooled portion of clones are prepared and hybridized to a second replica of the library. The hybridization pattern on the first and second replicas of the library are compared and cross-hybridizing clones, other than the clones in the pooled column and row, that hybridize to identical clones in the first and second replicas are identified. These clones necessarily include DNA inserts that overlap with the DNA insert int he common clone located at the intersection of the pooled row and pooled column.

The DNA in the entire library may be mapped by pooling the clones in each of the rows and columns of the matrix, preparing mixed end-specific probes and hybridizing the probes from each row or column to a replica of the library. Since all clones in the library are located at the intersection of a column and a row, the overlapping clones for all clones in the library may be identified and a physical map constructed.

In other preferred embodiments, the cosmid clones are arranged in a three dimensional matrix, pooled and compared in threes according to intersecting planes of the three dimensional matrix. Arrangements corresponding to geometries of higher dimensions may also be prepared and used to simultaneously identify overlapping clones in highly complex libraries with relatively few hybridization reactions.

28 Claims, 7 Drawing Sheets

Contig #2:

```
17,6           -->      3,12
17,6  --> 10,16
          10,16 --> 3,12
                  3,12 --> 19,27
                 19,27 --> 3,12
                         3,12 --> 10,6
                                10,6 <-- 1,3
                                        1,3 <-- 10,1
                                               10,1 --> 2,20
         14,23 <-- 3,12
  3,12 <-- 14,23
```

PHYSICAL MAPPING OF COMPLEX GENOMES

This invention was made with Government support under Grant No. R01 HD 18012 awarded by the National Institutes of Health and Contract No. DE-FG03-88ER60694 awarded by the Department of Energy. The Government has certain rights in this invention.

RELATED APPLICATIONS

This application is related to the patent application U.S. Ser. No. 039,509, filed Apr. 17, 1987 and its continuation-in-part application U.S. Ser. No. 181,836, filed Apr. 15, 1988, both of which are expressly incorporated herein by reference.

FIELD OF THE INVENTION

The present invention relates to a method of recombinant DNA technology. More particularly, the invention concerns a process for physical mapping of large complex genomes, including human chromosomes. The process ("multiplex analysis") is an alternate strategy for "bottom-up" mapping, and depends on the use of cosmid vectors containing endogenous bacteriophage promoters to allow for the identification of overlapping clones by hybridization with RNA probes synthesized directly from the DNA fragments inserted therein. Since the recognition of overlaps is not based on pattern recognition, analysis may be carried out simultaneously on cosmid clones grouped together.

BACKGROUND OF THE INVENTION

The complete analysis of large complex genomes, such as genomes of higher eukaryotes, including human, requires the extensive isolation, purification and analysis of large fragments of DNA by cloning, generally in *E. coli*. In the past, the lambda bacteriophage cloning system has been used most frequently to generate genomic libraries. The lambda bacteriophage vectors usually accommodate inserts up to about 20 kb. Presently the primary system used to clone and manipulate large DNA fragments is that of cosmid vectors. Cosmid vectors allow the packaging of DNA fragments of up to about 45 kb in plasmids containing bacteriophage cos sites for in vitro packaging.

The analysis of complex genomes involves the application of both "top-down" and "bottom-up" mapping strategies. The "top-down" strategy depends on the separation on pulsed field gels of large DNA fragments generated using rare restriction endonucleases for physical linkage of DNA markers and the construction of long-range maps [Schwartz et al., *Cell* 37, 67 (1984); Southern et al., *Nucleic Acids Res.* 15, 5925 (1987); Burke et al., *Science* 236, 806 (1987)] The "bottom-up" strategy depends on identifying overlapping sequences in a large number of randomly selected bacteriophage or cosmid clones by unique restriction enzyme "fingerprinting" and their assembly into overlapping sets of clones. "Top down" mapping is inherently more rapid and less labor intensive but does not generate sets of DNA clones for further structural or biological analysis. "Bottom-up" mapping generates the required sets of overlapping clones but application of current strategies and pattern matching algorithms to mammalian genomes will require the analysis of thousands to tens of thousands of individual clones for the generation of complete maps.

In the past few years, "bottom-up" mapping strategies have been successfully applied to generate complete or partial genomic maps of *E. coli, C. elegans* and *S. cerevisiae*.

Olson et al., *Proc. Natl. Acad. Sci. USA* 83, 7826 (1986), fingerprinted 5000 randomly selected lambda clones containing inserts of about 15 kb of genomic DNA from *S. cerevisiae*, by measuring the restriction fragment lengths obtained upon double digestion with EcoRI and HindIII. They used a pattern matching algorithm to construct overlapping sets of clones (contigs) extending over about 60% of the *S. cerevisiae* genome.

Coulson et al., *Proc. Natl. Acad. Sci. USA* 83, 7821 (1986) adopted a somewhat different methodology to construct a physical map of the genome of Caenorhabditis elegans, a nematode having a genome of approximately $8 \times 10^7$ base pairs. They digested cosmid DNAs with the restriction enzyme HindIII having a 6-bp specificity, filled the 5'-overhang with radioactive nucleotides, digested with the 4-bp specific enzyme Sau3A, and determined the size of the labeled fragments by electrophoresis in a sequencing gel followed by autoradiography. The mean size of the DNA inserts in the cosmid vectors was about 34 kb. Eight hundred sixty clusters of clones, totaling about 60% of the Caenorhabditis elegans genome, have been characterized.

Kohara et al., *Cell* 50, 495 (1987) analyzed 1025 lambda phage clones containing about 15.5-kb inserts of genomic *E. coli* DNA. For each clone they constructed a complete restriction map by means of eight restriction enzymes. The data for the 1025 clones were processed and sorted into 70 groups, including seven standing alone clones representing about 94% of the entire genome of *E. coli*.

While effective, the application of these "fingerprinting" and pattern matching strategies to mammalian genomes would require the individual analysis of tens or hundreds of thousands of clones for map construction as well as highly efficient computer algorithms for pattern recognition. Moreover, these and similar "fingerprinting" protocols require substantial amounts of overlap of 5 to 25% for the overlapping region to be detected. A theoretical analysis of "fingerprinting techniques" has suggested that the efficiency of the analysis is strongly dependent on the criteria used to declare overlaps between clones. According to Lander et al., *Genomics* 2, 231 (1988), the minimum detectable overlap has a major effect on the progress of the mapping project. Reducing the degree of overlap required for detection would substantially decrease the number of the clones which must be analyzed to obtain map closure.

Another way of detecting overlaps is the identification of overlapping clones by hybridization with RNA probes instead of pattern recognition. The identification of several bacteriophage-encoded RNA polymerases and the sequencing of their promoters has spawned a new technology for producing RNA probes. Cloning vectors are now available in which the promoters for a single polymerase, or for two different polymerases, lie adjacent to a cloning site. Transcription with any of the available polymerases enables one to produce large quantities of high-specific activity RNA probes which correspond to either the coding or the non-coding strands [Wahl et al., Methods in Enzymology 152, 572 (1987)].

Wahl et al., *Proc. Natl. Acad. Sci. USA* 84, 2160 (1987) (see also U.S. Ser. No. 181,836 filed Apr. 15, 1988) have designed special cosmid vectors for rapid genomic "walking" and restriction mapping. These vectors (designated as pWE for "walking easily") contain the transcription promoters from either bacteriophage SP6, T7, or T3 flanking a unique cloning site for the insertion of genomic DNA fragments. These vectors allow the synthesis of end-specific RNA probes directly from the DNA inserts, and are suitable for the detection of overlapping regions of several hundred bp in contiguous cosmids.

One practical limitation of cloning in cosmid vectors, including the above pWE vectors, is that most vectors require the initial preparation of very high quality genomic DNA, digestion to appropriate size range for cloning, and the careful purification of appropriately sized DNA fragments on gradients or gels [DiLella et al., *Methods in Enzymology* 152, 199 (1987)]. In the traditional cosmid cloning procedure, linearized cosmid vectors are dephosphorylated to avoid concatamerization, prior to ligation to the DNA fragments. Since the DNA inserts cannot be dephosphorylated, their size fractionation is unavoidable to avoid recombinational rearrangements caused by multiple inserts ligated into a single cosmid. For these manipulations, a substantial quantity of genomic DNA is required to construct a representative genomic library, and cosmid cloning has not been practical in situations where only submicrogram amounts of DNA can be isolated. Bates et al. *Gene* 26, 137 (1983) described cosmid vectors with two cos sites separated by a blunt-end restriction enzyme site. They found that the double cos-site vectors eliminate the need to prepare two separate cosmid arms, and the internal blunt-end restriction site prevents cosmid concatamerization. Thus, a double restriction enzyme digestion was found to be sufficient to prepare a vector for subsequent ligation with DNA fragments which were dephosphorylated to prevent their self-ligation. This technique eliminated the need to purify insert DNA of the proper size (30-45 kb).

The use of cosmid vectors with two or more cos sites has been shown to simplify the cloning procedure by eliminating complex preparation of cloning "arms" by Ehrich et al. in *Gene* 57, 229 (1987).

A. Cosmids prepared in vector sCOS-1 or one of its derivatives can be used to synthesize end-specific probes for the detection of overlaps.

B. Cosmid clones are inoculated on the surface of a nitrocellulose or nylon filter from 96-well archive plates stored at $-70$ degrees. Each clone on the "grid" is assigned a unique identifying Y and X axis coordinate. Individual clones in the collection contain the innate capacity of generating probes specific for the extreme ends of the genomic DNA insert and detecting overlapping clones on the filter. The arrows show the locations of potential overlapping clones detected by hybridization of probes generated from the clone at coordinates $Y=2$, $X=7$.

C. and D. To enable analysis of multiple clones simultaneously, cosmids are pooled according to the rows and columns of the matrix, DNA prepared and a mixed RNA probe synthesized. When hybridized to the matrix filter, the probe detects a pattern of spots consisting of all of the template clones and the collection of clones overlapping with one end of each of the template clones. A similar procedure is carried out using cosmids pooled according to columns of the matrix. When the two data sets are compared, hybridizing clones identified by both of the mixed probes may be overlapping with the template clone common to both sets: that clone located at the intersection of the row and column. This procedure may then be repeated using other combinations of pooled probes and either T7 or T3 polymerase. The arrows denote the location of a clone which overlaps with the "T7 end" of the clone at coordinates $Y=2$, $X=4$.

Figure 5B:
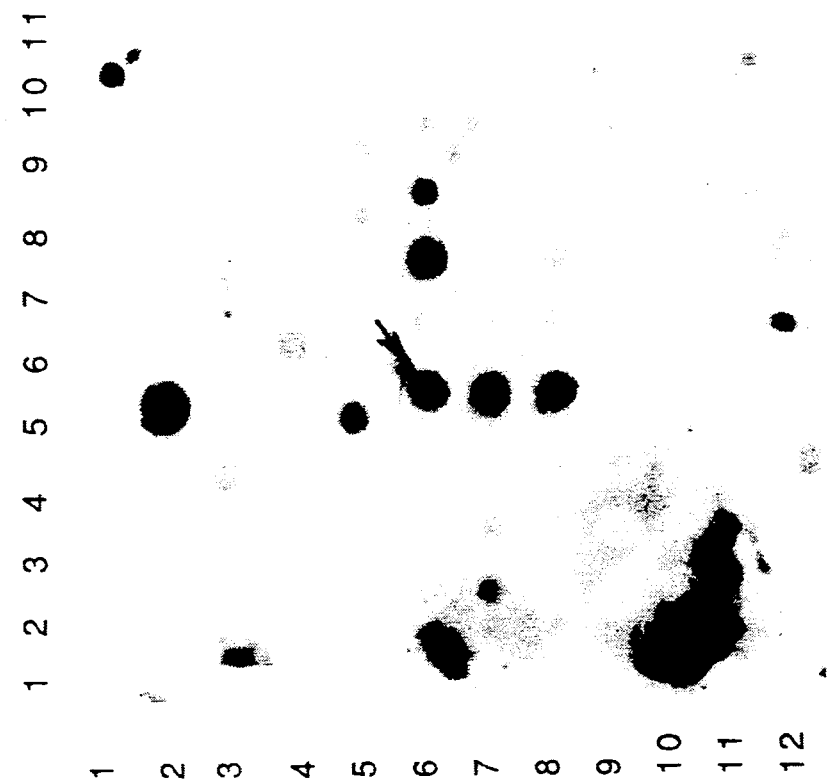
Figure 5A:
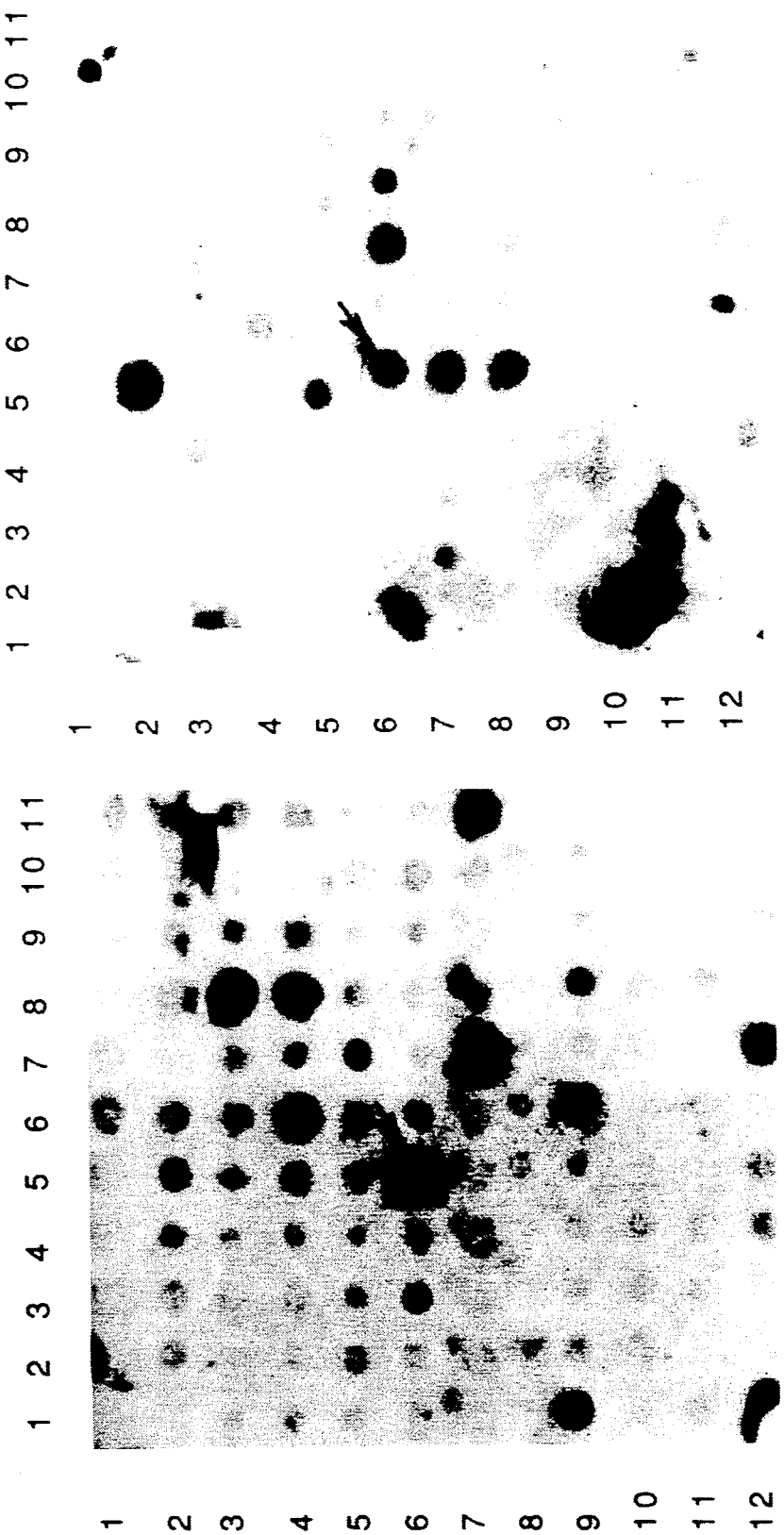

FIG. 5 shows the cosmid multiplex analysis of a collection of cosmids mapping to the long arm of human chromosome 11.

A. Multiplex analysis of human cosmid clones arrayed in a $36\times36$ matrix and hybridized with a mixed probe consisting of RNA transcripts from clone of a row of the matrix. A portion of the filter is shown.

B. A portion of the filter shown in A hybridized with a mixed probe representing a pool of all cosmids aligned along a column of the matrix. The arrow identifies a cosmid clone which hybridizes with both mixed probes and is linked to the clone located at the intersection of the row and column from which probe mixtures were prepared.

Figures 6A, 6B:
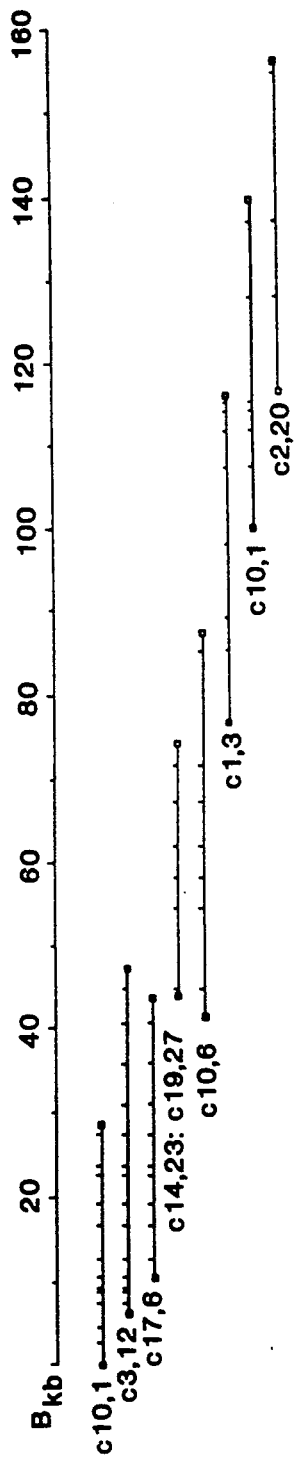

FIG. 6 shows predicted contigs from human chromosome 11q and restriction enzyme digestion analysis.

A. Predicted linkage and orientation of a representative cosmid contig generated by multiplex analysis of the chromosome 11q cosmid set and data analysis using the computer program "Contig-maker". The computer output indicates the coordinates of linked clones (X,Y) and the arrows denote the orientation of the linkage.

B. Restriction map and location of probes used to establish unequivocal overlap of the cosmids. A restriction map of the overlapping clones detected in A was determined by the analysis of partial EcoRI digestion products hybridized with $^{32}$P-labeled T3 or T7 promoter-specific oligonucleotides. Overlapping areas not confirmed by restriction map analysis were confirmed by hybridization analysis using end-specific RNA probes generated from individual cosmid clones. Cosmid clones c14,23 and c19,27 are identical. □ indicates bacteriophage T3 promoter, ■ bacteriophage T7 promoter.

SUMMARY OF THE INVENTION

The present invention relates to a rapid and powerful method for "bottom-up" mapping that is applicable to mammalian chromosomes and allows for the simultaneous analysis of multiple cosmid clones for the detection of overlaps. The method, called "cosmid multiplex analysis", depends on the use of cosmid vectors allowing for the synthesis of corresponding RNA sequences (probes) specific to the extreme ends of the DNA fragments inserted therein, directly from the DNA inserts. In this way, rather than depending on "fingerprinting" procedures for detection of overlapping clones, cosmid libraries are constructed using vectors containing at least one bacteriophage promoter adjacent to the genomic DNA insert, positioned operatively for the transcription thereof. Preferably, the cosmid vectors contain two bacteriophage promoters flanking the DNA fragment ligated into the insertion site. Synthesis of an end-specific RNA probe from any clone in the collection allows the overlapping clones to be easily detected by hybridization. Because this strategy does not depend on pattern recognition for detecting overlaps, analysis may be carried out simultaneously on cosmid clones grouped together. The method is suitable for the unambiguous detection of overlapping regions as small as several hundred nucleotides in contiguous cosmids. Accordingly, the number of clones needed for map closure can be reduced by up to three-fold. Finally, this strategy represents essentially simultaneous cosmid "walking" and thus is basically non-random, allowing the investigator the freedom to pause and investigate some interesting biology rather than requiring completion of the map before it becomes useful.

In one aspect, the present invention relates to a process for simultaneous analysis of multiple cosmid clones, comprising:

(1) synthesizing mixed end-specific RNA sequences directly from DNA templates prepared from groups of cosmid clones pooled together, (2) hybridizing the mixed end-specific RNA sequences derived from individual groups of cosmid clones to a replica of all cosmid clones to be analyzed, whereby a data set of hybridization spots corresponding to all of said DNA templates and the collection of DNAs overlapping with one end of each of the DNA templates is identified, (3) identifying cross-hybridizing clones which are common to two or more data sets.

In a preferred embodiment, the cross-hybridizing clones are identified by pairwise comparison of data sets obtained from two groups of cosmid clones containing at least one common clone. The cosmid clones are preferably pooled according to the rows and columns of a two-dimensional matrix.

In a further aspect, the invention relates to a process for physical mapping of complex genomes, comprising:

(1) generating a genomic library of clones in cosmid vectors allowing for the synthesis of end-specific RNA sequences directly from at least one end of a DNA fragment inserted therein, (2) providing groups of cosmid clones pooled together, (3) synthesizing mixed end-specific RNA sequences directly from DNA templates prepared from said groups of cosmid clones, (4) hybridizing the mixed end-specific RNA sequences derived from individual groups of cosmid clones to a replica of all cosmid clones to be analyzed, whereby a data set of hybridization spots corresponding to all of said DNA templates and the collection of DNAs overlapping with one end of each of the DNA templates is identified, (5) identifying cross-hybridizing clones which are common to two or more data sets, and (6) assembling contigs of said cross-hybridizing clones.

In a preferred embodiment, the cosmid vectors used in the above processes comprise two oppositely oriented promoters, each of which is specific for a bacteriophage RNA polymerase, positioned on two sides of the cloning site. Most preferably, the vectors contain T3 and T7 endogenous bacteriophage promoters flanking the cloned genomic DNA. Vectors containing at least two cos sites are particularly preferred, since they allow the use of DNA fragments without previous size separation.

From the list of linked clones produced by this technique, contigs can be assembled either manually or through computer analysis of the data.

DETAILED DESCRIPTION OF THE INVENTION

Definitions

"Genomic library" is a mixture of clones constructed by inserting fragments of genomic DNA into a suitable vector. The term "library" implies the existence of large numbers of different recombinants out of which only a few are of immediate interest to the investigator.

The terms "cosmid" and "cosmid vector" and grammatical variations thereof, are used interchangeably and refer to plasmid vectors that contain a lambda bacteriophage cos (cohesive end) site. The lambda bacteriophage packaging system selects DNA molecules of about the size of the lambda genome (37–52 kb). Accordingly, plasmid recombinant DNA having a minimum size of about 38 kb and a maximum size of about 52 kb (about 78% and about 105% of phage lambda, respectively), can be packaged in vitro in the lambda phage coat. In addition to the cos site(s) cosmid vectors usually contain a marker gene allowing for selection in bacteria (antibiotic resistance gene), and one or more unique restriction sites for cloning. Plasmids with a large variety of cloning sites and prokaryotic and eukaryotic selection markers can be converted to cosmids by insertion of the lambda cos region.

The term "plasmid" refers to circular, double-stranded DNA loops which in their vector form, are not bound to the chromosome.

As used herein, the term "a promoter specific for a bacteriophage RNA polymerase" means a wild-type or non-wild-type promoter that can be used by the bacteriophage RNA polymerase for in vitro transcription of a DNA fragment. When a non-wild-type promoter is used for such in vitro transcription of a DNA fragment, transcription will occur at a rate which is at least 10% of the rate at which transcription would have occurred if a wild-type or native promoter had been used by the bacteriophage RNA polymerase to transcribe the DNA fragment in vitro.

The term "cloning site" as used herein, means restriction endonuclease site on the DNA sequence of the cosmid vectors of the present invention where a DNA fragment can be inserted without deleting any of the original DNA.

The term positioning a promoter "operatively for transcription of a DNA fragment" as used herein, means that the promoter will be positioned in such a way that any DNA sequences between the promoter's transcriptional start site and the DNA fragment will not prevent transcription of at least a portion of the DNA fragment by the promoter. The term "at least a portion" means that preferably at least 8bp and more preferably at least about 30 bp of the DNA fragment will be transcribed.

The terms "end-specific RNA sequences", "RNA probes", and grammatical variations thereof, are used to refer to hybridization probes obtained by transcription of corresponding DNA fragments.

Clones are overlapping if they contain contiguous DNA in the same relationship as that in the genome. One method for detecting overlaps is to synthesize an RNA probe from one end of a first clone. If this probe detectably hybridizes with an end of the second clone under standard hybridization conditions, the two clones are overlapping [Wahl et al., PNAS USA 84, 2160 (1987)].

The term "contig" was introduced by Rodger Staden, Nucleic Acids Res. 8, 3673 (1980) in connection with DNA sequence analysis, and refers to groups of clones with contiguous nucleotide sequences.

Materials and General Methods

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987).

Cell lines

TG 5D1-1 is a Friend cell line derived from somatic cell hybrid 5D1 that carried an intact human X chromosome 11 [Pyati et al., Proc. Natl. Acad. Sci USA 77, 3435 (1980)], and was selected for the loss of the entire X chromosome and most of chromosome 11. TG 5D1-1 contains the distal portion of chromosome 11 as the only human material in a mouse genomic background [Maslen et al., Genomics 2, 66 (1988)]. Cytogenetic and molecular analysis indicates that the amount of human DNA represented about 1% of the mouse genomic background [Maslen et al., Supra].

Bacterial Strains

Cosmid vectors were replicated in E. coli strain DH5, a derivative of the strongly recA. strain DH1 (commercially available, e.g. from Bethesda Laboratories, Gaithersburg, Md., USA), in AG1 (Stratagene Cloning Systems, San Diego, Calif.) a derivative of DH5 selected for high packaging efficiency, or in HB101 (commercially available, e.g. from Bethesda Laboratories, Gaithersburg, Md., USA).

Cosmid Vectors

Figure 1:
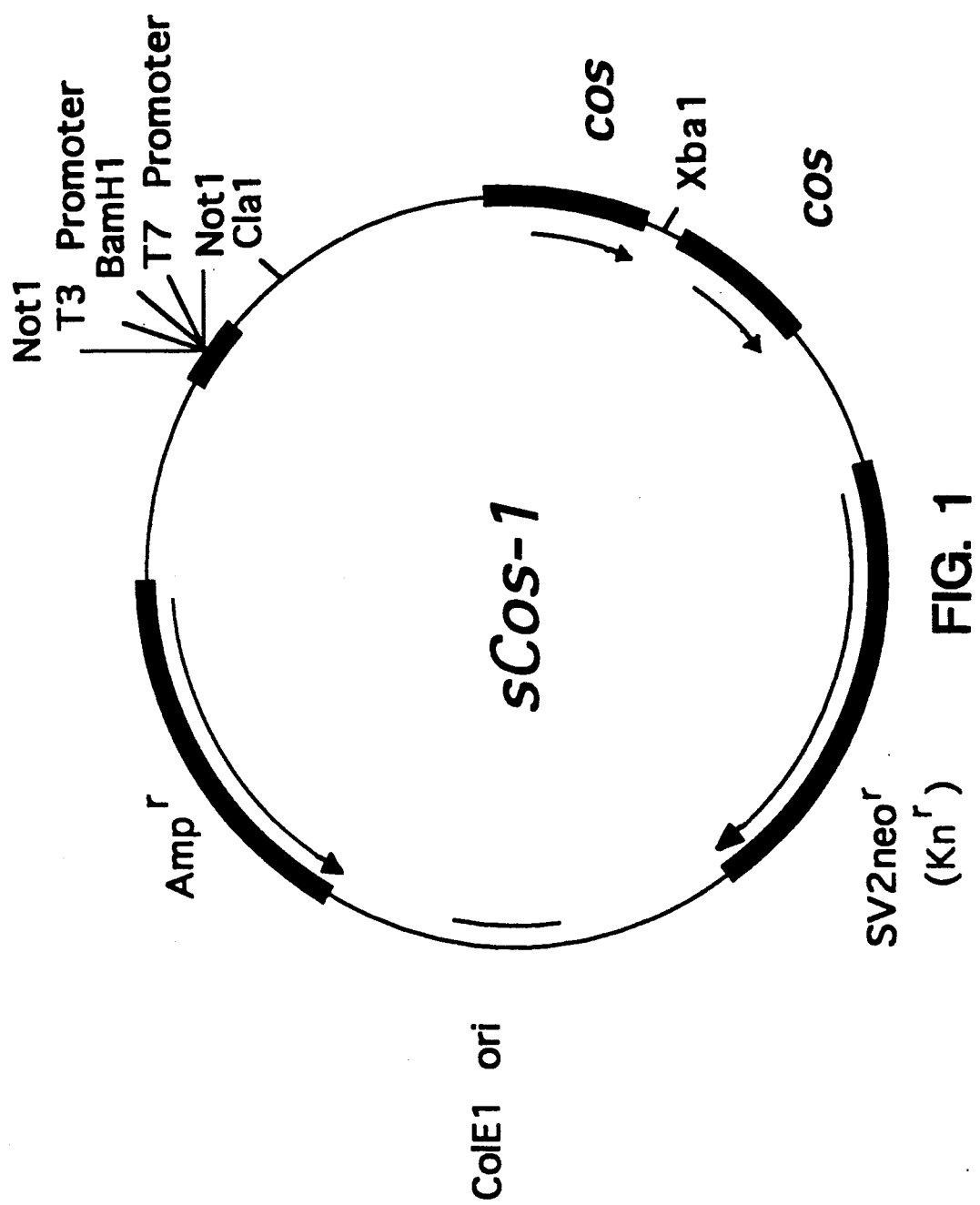
FIG. 1 shows the vector sCOS-1 designed for cosmid multiplex analysis. The vector contains bacteriophage T3 and T7 promoters flanking a unique BamHI cloning site, NotI sites for expedited restriction mapping and excision of the insert DNA, duplicated cos sites for high efficiency microcloning, a dominant selection for transfection into mammalian cells, Amp and Kn resistance genes, and ColE1 origin of replication.
Figure 2:
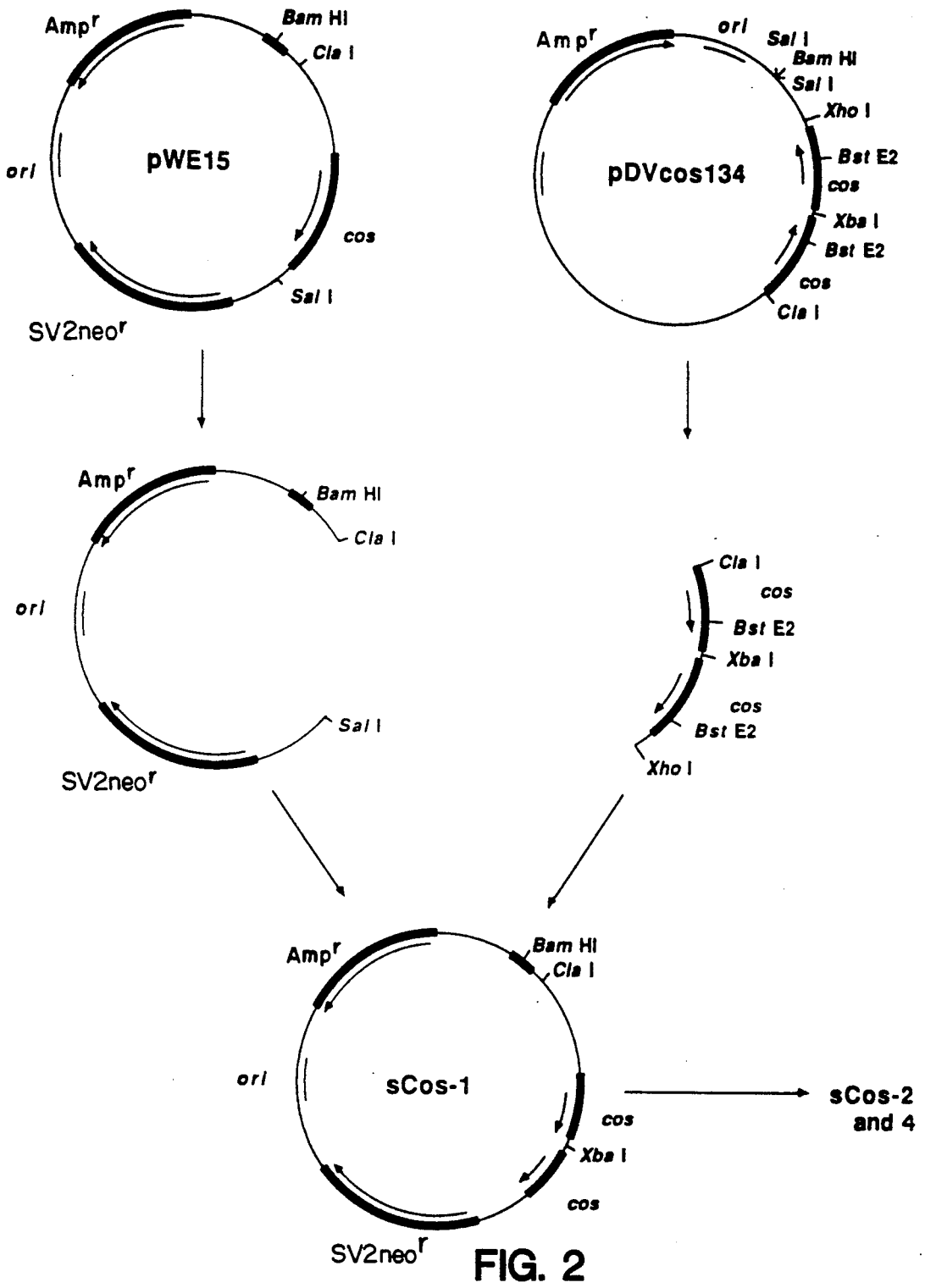
FIG. 2 illustrates the construction of cosmid vector sCOS-1. Relevant restriction sites in the precursor molecules are shown. ClaI-SalI and CalI-XhoI fragments were excised from pWE15 and pDVcos143 and purified on agarose gels. The indicated fragments were joined using T4 DNA ligase and coligation of the XhoI and SalI sites resulted in the loss of both sites in the resulting plasmids.

Genomic libraries were constructed in cosmid vector sCOS-1 illustrated in FIG. 1. sCOS-1 was prepared from cosmid vectors pWE15 [Evans et al., Methods in Enzymology 152, 604 (1987) and U.S. Ser. No. 181,836, ATCC Accession No. American Type Culture Collection (ATCC), 12301 Parklawn Drive, Rockville, Md. 20852 U.S.A. 37503] and pDVcos134 [a gift from J. Reese, in wide circulation among scientists] as shown in FIG. 2. pWE15 DNA was digested with ClaI and SalI, and the 6 kb ClaI-SalI restriction fragment, lacking the cos sequence was purified. Cosmid pDVcos134 was digested with ClaI and XhoI and a restriction fragment containing the duplicated cos region was purified on a low melting point agarose gel. The purified fragments were ligated using T4 DNA ligase and transformed into E. coli host strain DH5.

Other pWE plasmids suitable for genomic mapping according to the invention are disclosed in Evans et al., Methods in Enzymology, Supra and U.S. Ser. No. 181,836. Cosmid vector pWE16 has been deposited with the American Type Culture Collection, and has been accorded ATCC No. 37524.

Figure 3:
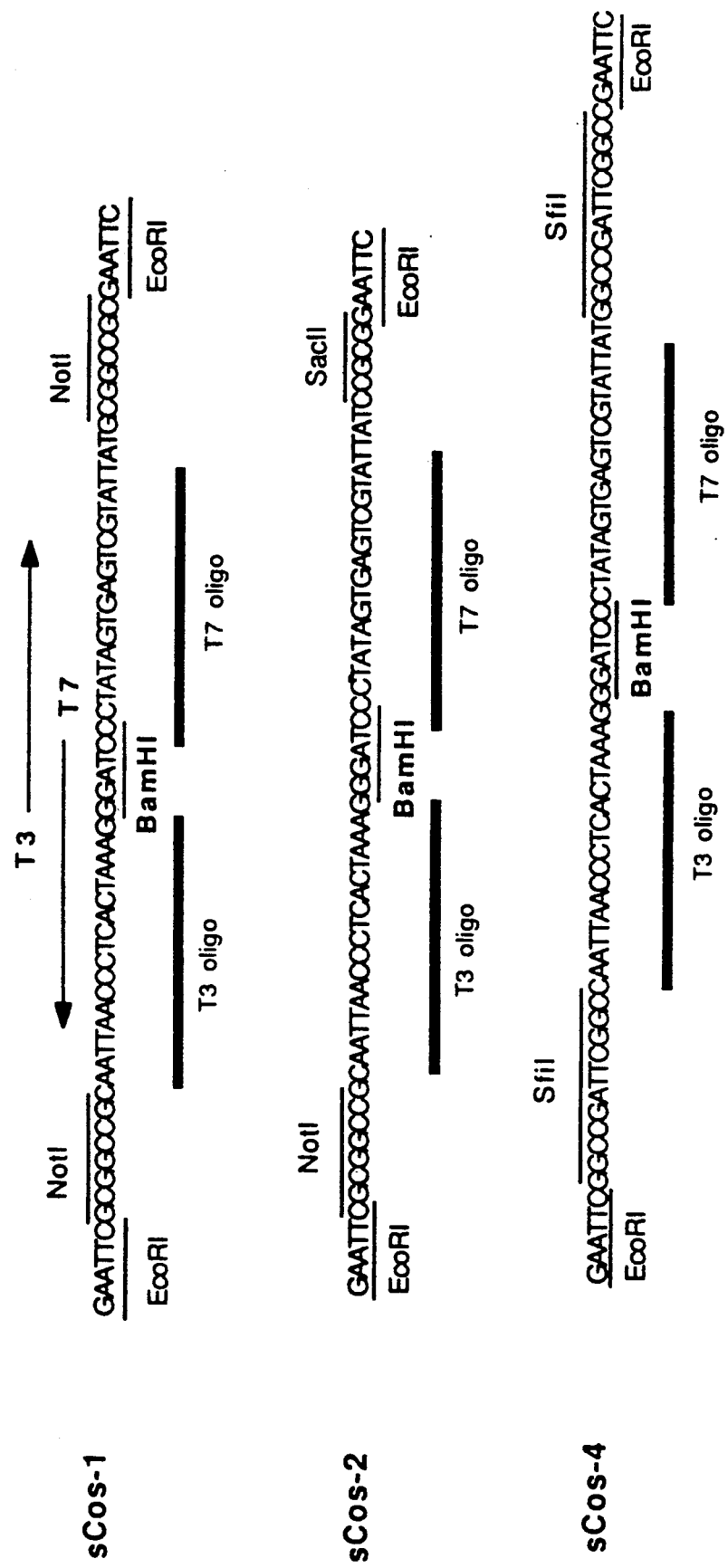
FIG. 3 depicts the DNA sequences of the cloning site, bacteriophage promoters and flanking restriction sites in sCOS vectors. Restriction sites and T3 and T7 promoter sequences added using synthetic oligonucleotides are shown. SfiI, NotI, EcoRI and SacII restriction sites are indicated by thin lines. The direction of transcription using T3 or T7 polymerase is indicated by the arrows and the thick lines delineate the critical nucleotides for promoter activity. The BamHI site is the cloning site into which MboI digested genomic DNA is inserted. All linkers were inserted by "linker-tailing" into the sites formed by digestion of sCOS-1 with EcoRI.

Cosmids sCOS-2 and sCOS-4 are derivatives of sCOS-1 where the cloning site has been altered to substitute other rare restriction sites for the NotI sites. Cosmid vector sCOS-2 was constructed by digesting sCOS-1 with EcoRI, and purifying the plasmid DNA away from the NotI-T3 promoter-BamHI-T7 promoter-NotI linker sequence by ethanol precipitat. A 30-nucleotide double-stranded synthetic oligomer with EcoRI coadhesive ends, containing NotI-T3 promoter-BamHI-T7 promoter-Sac2 sequences was added by linker-tailing [Lathe et al., DNA 3, 173 (1984)]. sCOS-4 was constructed using a similar procedure adding a double-stranded synthetic oligonucleotide containing EcoTI coadhesive ends and a SfiI-T3 promoter-BamHI-T7 promoter-SfiI sequence. The sequences of the linker-cloning promoter sequences of sCOS vectors are shown in FIG. 3.

Construction of Cosmid Libraries In sCOS Vectors

High molecular weight genomic DNA for cosmid cloning was prepared by proteinase k digestion and gentle phenol extraction followed by dialysis [DiLella et al., Methods in Enzymology 152, 199 (1987)]. The average molecular size of the isolated DNA was determined using field inversion gel electrophoresis [Carle et al., Science 232, 65 (1986)] and ranged from about 500 kb to greater than 3 mb. DNA was digested with MboI under conditions recommended by the manufacturers and the digestion terminated by phenol/chloroform extraction. Following digestion, the DNA was analyzed on field inversion gels or 0.3% agarose gels to determine the average size of the digestion products. For the construction of genomic libraries in cosmid vector sCOS-1 genomic DNA was digested to an average size of 100–120 kb, and dephosphorylated with calf intestinal phosphatase. The genomic DNA was not size separated before cloning.

Vector cloning arms were prepared by first digesting purified sCOS vector DNA with XbaI followed by dephosphorylation with calf intestinal alkaline phosphatase. The reaction was terminated by phenol/chloroform extraction and the DNA collected by ethanol precipitation. The linearized, dephosphorylated vector DNA was then digested with BamHI, extracted with phenol/chloroform and stored at a concentration of 1 mg/ml in 20mM TRIS.HCl, pH.6, 1 mM EDTA. Ligations were performed using 1 µg of vector arms and 50 ng to 3 µg of genomic DNA. Reactions were incubated with 2 Weiss Units of T4 DNA ligase and packaged using commercial in vitro packaging lysates. Bacteriophage lambda packaging extracts may contain significant amounts of EcoK restriction activity. To avoid the possibility that mammalian sequences containing an EcoK site might be underrepresented in the library, genomic libraries are prepared using in vitro packaging extracts which lack EcoK restriction activity (e.g. Gigapak-Gold; Stratagene Cloning Systems, San Diego, Calif.).

Cosmid libraries were plated directly on LB agar containing 25 µg/ml of kanamycin sulfate and libraries screened without further amplification [Evans et al., *Methods in Enzymology* 152, 604 (1987)]. Libraries were stored as original non-amplified plate stocks in LB media with 15% glycerol at a concentration of $2.2 \times 10^{11}$ bacteria/ml at −70 degrees. The cosmid library used in the study described in the examples consisted of $1.5 \times 10^7$ independent clones.

Selection of Human Clones from a Somatic Cell Hybrid Genomic Library

Cosmid libraries were plated on 570 cm$^2$ LB agar trays at a density of 10 clones/cm$^2$, replica filters prepared and filters hybridized with human placenta DNA labeled with $^{32}$P-dCTP to a specific activity of $10^8$ cpm/µg. Under these hybridization conditions, no background hybridization was detected against cosmids carrying mouse genomic DNA. Cosmids containing human genomic DNA inserts were picked with toothpicks, rescreened by hybridization to $^{32}$P-labeled human DNA, and archived in 96-well microtitre plates containing LB media, 15% glycerol and 25 µg/ml kanamycin sulfate at −70 degrees. Individual clones isolated from cosmid libraries were routinely grown, replicated, and DNA prepared using standard round-bottom 96-well microtitre plates. Replica transfer of clones in 96-well microtitre plates and transfer from archived plates to screening filters was carried out using an aluminum "hedgehog" made from 3-mm diameter brass rods set in plastic block, as described by Coulson et al., Supra (p. 7822), or a laboratory robot (Beckman Biomek 1000).

Plating and Screening Libraries

For multiplex analysis, archived cosmids were inoculated on the surface of a nitrocellulose or nylon based filter in a matrix or "grid" pattern. The size and density of the "grid" was determined by the pattern of wells in a standard 96-well microtitre plate and, in the experiments described in the examples, a $36 \times 36$ matrix was used. Before applying bacterial culture, a matrix pattern prepared on paper was transferred directly to the filter membrane by passing the filter through a copying machine followed by autoclaving. The clones were allowed to grow on the surface of the filter at 37 degrees for 12 to 15 hours and bacterial DNA was fixed to the filter using a standard colony lysis procedure [Vogeli et al., *Methods in Enzymology* 152, 407 (1987)].

RNA Probe Synthesis and Hybridization Reactions

Cosmids were transferred from archives to fresh 96-well plates containing liquid LB media with 25 µg/ml kanamycin sulfate and incubated at 37 degrees in a humidified atmosphere for 6 to 10 hours. Supernatants from individual wells were pooled and DNA prepared using a previously described cosmid miniprep procedure [Evans et al., *Methods in Enzymology*, Supra]. Cosmids constructed with vector sCOS-1, or one of its derivatives, yield up to 2 µg of DNA from a 300 µl culture and all probe synthesis and mapping reactions were carried out with DNA prepared from minilysates. In some cases, the pooled DNA was digested with a restriction endonuclease such as BamHI or HindIII prior to probe synthesis. RNA probes were synthesized as in patent applications U.S. Ser. Nos. 039,509 and 181,836 described, using bacteriophage T3 or T7 polymerase (Stratagene Cloning Systems, San Diego, Calif., USA). Briefly, cosmid DNA was prepared and 1-2 µg of the DNA was transcribed with T7 or T3 RNA polymerase in a 20 µl reaction, as described by Melton, et al. (1984) *Nucleic Acids Res.* 12: 7035-7054, using 50 µCi of [$\alpha$-$^{32}$P] UTP and 12 µM unlabeled UTP. $^{32}$P-UTP and polymerase reactions were terminated by extraction with phenol and chloroform. 100 µl of blocking mixture (a mixture of sonicated human placenta DNA and cloned human repetitive sequences at a concentration of 1 mg/ml) was added, and the probe mixture was precipitated with ethanol. The nucleic acid was then resuspended in 20 µl of 5X SSPE, 0.1% SDS, and prehybridized for 5 minutes at 42 degrees to saturate repetitive sequences which might be present in the probe. The probe was then added to a plastic bag containing a replica of the matrix filter and hybridization buffer [5X SSPE, 50% formamide, 0.2% SDS, 1× Denhardt's solution (D. Denhardt, *Biochem. Biophys. Res. Commun.* 23, 641 (1966)), and 20 µg/ml salmon sperm DNA] and the hybridization reaction carried out for 12 to 18 hours. Filters were washed in 0.1× SSPE, 0.1% SDS, at 65 degrees and exposed to X-ray film for 2 to 8 hours.

Restriction Enzyme Analysis

Restriction enzyme analysis of isolated cosmids was carried out using DNA isolated from minilysates. Cosmid DNA was prepared from minilysates as follows:

DNA was isolated from 1.5 ml cultures. A culture was inoculated with a single bacterial colony and incubated with vigorous shaking at 37 degrees for 6 hours. DNA was prepared using a modified boiling procedure [Evans et al., *Methods in Enzymology* 152, 604 (1987)]. Cells were collected by a brief (1 min.) centrifugation in a microcentrifuge and cells were resuspended in 300 µl of STET buffer. 20 µl of freshly prepared lysozyme (10 mg/ml) in STET buffer were added, the mixture vortexed and incubated in a boiling water bath for one minute. The solution was immediately centrifuged for 10 minutes in a microcentrifuge and the gelatinous pellet removed with a toothpick and discarded. 325 µl of isopropanol were added and the mixture incubated at room temperature for 5 minutes. The precipitated DNA was collected by centrifugation at room temperature in a microcentrifuge, the pellet dried and resuspended in water.

DNA was digested to completion with NotI, digested partially with one or more enzymes (typically BamHI, EcoHI, HindIII, SacII, PvuII, and KpnI), separated on an agarose gel, transferred to a nitrocellulose filter and hybridized with $^{32}$P-labeled oligonucleotides recognizing the T3 or T7 bacteriophage promoters. T3 and T7 oligonucleotides (commercially available as sequencing primers, Stratagene Cloning Systems, San Diego, Calif., USA) were labeled using polynucleotide kinase and $\gamma$-$^{32}$P ATP to a specific activity of $2 \times 10^8$ cpm/$\mu$g. The labeled oligonucleotides were then hybridized to the filters in $6\times$ SSC, 10% Denhardt's solution for 12 hours at 42 degrees and washed in $2\times$ SSC for 10 minutes at 50 degrees. Filters were exposed to X-ray film for 20 minutes to 12 hours. The pattern of bands appearing on the autoradiograph could then be interpreted as indicating the distance from the cloning site to the restriction site, much as with the "cos"-mapping procedure of Rackwitz et al., Gene 30, 195 (1984).

Alternatively, programmed automatic restriction enzyme digestions were carried out to completion in 96-well microtitre plates using a laboratory robot (Beckman Biomek 1000).

Data Analysis

The resulting hybridization data were manually entered into a computer file and analyzed using two computer programs written by G. A. Evans in Turbo Pascal (Borland International) running on Apple Macintosh II or Macintosh SE computers. One program "Multiplex-mapper" compared data sets from hybridization reactions using mixed probes, determined those clones which were identified by more than one probe mixture, and produced a list of linked clones. A second program, "Contig-maker" assembled the list of overlapping clones into potential contigs which could be analyzed in greater detail. In some cases, orientation and overlap of individual cosmid clones in a contig were confirmed by detailed restriction mapping and hybridization analysis of the individual cosmid clones.

Although data analysis was performed using the above-mentioned computer programs, a person of ordinary skill in the art should have no difficulty in carrying out the comparison of data and assembling the overlapping clones into contigs using other software. Moreover, manual data comparison and contig making are also possible, though more laborious.

LB media 10 g Bacto-tryptone, 5 g yeast extract, 5 g NaCl per lit. of water. Autoclave.

LB agar LB media containing 1.2% Bacto-agar. Autoclave.

STET buffer 50 mM TRIS.HCl, pH 8.0, 8% sucrose, 5% Triton X-100 and 50 mM EDTA

Denhardt's solution 0.2% Ficoll, 0.2% polyvinyl pyrrolidone, 0.2% bovine serum albumin

Abbreviations

SDS: sodium dodecyl sulfate
SSPE: saline sodium phosphate EDTA
SSC: saline sodium citrate

DESCRIPTION OF THE PREFERRED EMBODIMENTS

The present invention relates to a new approach for "bottom-up" genomic mapping using cosmid clones. It has been found that significant improvements in the speed and efficiency of "bottom-up" genomic mapping can be achieved, by 1) isolating restricted regions of large mammalian genomes in a "sublibrary" preorganized on a solid matrix, 2) using hybridization of end-specific probes for detection of overlapping clones in the collection, rather than "fingerprinting" followed by pattern recognition, and 3) analyzing multiple clones simultaneously for the detection of all overlaps in the collection.

According to the invention, essentially the strategy illustrated in FIG. 4 is used for genomic mapping using cosmid vectors.

In a first step, a genomic library which represents a limited portion of a genome is constructed in a cosmid vector allowing for the synthesis of RNA probes directly from insert DNA using endogenous bacteriophage promoters. A convenient and powerful way of subdividing the human genome for the preparation of libraries is through chromosome purification by flow cytometry [Gray et al., Cold Spring Harbor Symp. LI 1986 p. 141].

Preferred cosmid vectors suitable for constructing a genomic "sub-library" include the pWE vectors described by Wahl et al., Proc. Natl. Acad. Sci. USA 84, 2160 (1987), e.g. pWE2, pWE4, pWE8 pWE10, pWE15, and pWE16, preferably pWE15 and pWE16. The construction of these vectors is described in the Materials and Methods section of the cited article, in Evans et al., Methods in Enzymology 152, 604 (1987), and in the copending U.S. patent application Ser. No. 181,836. These vectors, in addition to replication and selection functions, such as plasmid origin of replication, bacterial genes specifying antibiotic resistance, and the bacteriophage lambda cohesive termini (cos sequences), contain the transcription promoters from either bacteriophage SP6, T7, or T3 flanking a unique BamHI cloning site. This design allows for rapid production of RNA probes specific for both ends of the inserted DNA sequences.

A practical limitation of the use of the pWE cosmid vectors is that they, as most other cosmid vectors, require the initial preparation of very high quality genomic DNA, digestion to appropriate size range for cloning, and the careful purification of appropriately sized DNA fragments on gradients or gels. Accordingly, these vectors cannot be used in situations where only submicrogram amounts of DNA can be isolated. To address this problem, new cosmid vectors containing a duplicated cos sequence have been designed and constructed. These "sCOS" vectors have the following important characteristics: 1) the presence of two cos sites such that packaging could be carried out with high efficiency and without requiring size selection of the insert DNA; 2) the presence of T3 and T7 bacteriophage promoters for the synthesis of "walking" probes; 3) unique restriction sites for removing the insert and to aid in restriction mapping; 4) selectable genes for gene transfer in eukaryotic cells, and 5) a plasmid origin of replication giving a high yield of cosmid DNA for preparing templates. The construction of the plasmid sCOS-1 is described in the Materials and General Methods section of the specification, and is illustrated in FIGS. 1 and 2. As hereinabove described, cosmid sCOS-1 was constructed by coligating a 6 kg ClaI-SalI fragment of the cosmid vector pWE15 that contains the ColE1 origin of replication, beta lactamase, SV2-neo gene, cloning and bacteriophage promoter sites, with a 1.6 kb ClaI-XhoI fragment excised from cosmid vector pDVcos134. This fragment contains a duplication of the cos packaging signal from bacteriophage vector Charon 4A separated by a unique XbaI site. This fragment contains a complete duplication of the sites for nicking cosN and binding cosB of bacteriophage lambda terminase as well as flanking sequences [Friess et al., Gene 24, 207 (1983)]. The resulting plasmid vector, shown in FIG. 1, is 6.7 kb in size and has a cloning capacity of 31 to 48 kb. As with pWE vectors, bacteriophage T3 and T7 promoters were oriented into the BamHI cloning site to allow direct synthesis of end-specific RNA probes for molecular "walking". Previous experience with pWE cosmids suggested that NotI restriction sites may not be ideal for excision or mapping of inserts in some regions of the genome where NotI sites might be clustered. Therefore, additional cosmid vectors with other rare restriction sites have been constructed, by substituting the cloning/polymerase sites of sCOS-1 with sequences containing NotI and SacII sites (sCOS-2) or SfiI sites (sCOS-4). The asymmetric rare sites in sCOS-2 are useful for cloning ends of large NotI or SacII fragments for isolation of "linking" clones for long range mapping by pulsed field gel analysis [Buiting et al., Genomics 3, 143 (1988)]. Also, vectors which lack NotI sites, such as sCOS-4, would potentially allow the selection of clones containing unique NotI junction fragments by hybridization with NotI-specific oligonucleotides Estivill et al., Nucleic Acids Res. 15, 1415 (1987)].

While the use of cosmid vectors with two or more cos sites has previously been shown to simplify the cloning procedure by eliminating complex preparation of cloning arms [Ehrich et al., Gene 57, 229 (1987)], it has been unexpectedly found that these vectors have cloning efficiencies one or two orders of magnitude greater than similar vectors with a single cos site. Preparation of cosmid libraries with these vectors also allows dephosphorylation of the genomic DNA to prevent ligation of non-contiguous fragments into concatamers. Due to the greatly increased cloning efficiencies and to the avoidance of size separation of genomic DNA and consequential losses in material, the double cos site sCOS vectors make feasible the preparation of representative libraries from very small amounts of purified, partially digested DNA, and are, therefore, preferred for carrying out the present invention.

The individual clones of the genomic library are arranged on a nitrocellulose or nylon filter matrix and each clone is identified by unique coordinates. If the randomly chosen clones are arranged in a two-dimensional matrix, they are identified by unique X and Y coordinates. For convenience in handling, the pattern of the matrix is preferably based on the pattern and spacing of wells of a standard 96-well microtitre plate and the repetitive preparation of culture plates and hybridization filters may be carried out using equipment designed for working with this standard. Each individual cosmid clone in the collection possesses the innate mechanism of generating an RNA probe capable of detecting any overlapping or identical clones in the collection.

If DNA is prepared from individual clones, an RNA probe generated using T3 or T7 polymerase, and overlapping clone detected by hybridization of the probe to a replica of the filter grid, using cosmid clones arranged on a 36×36 matrix containing 1296 clones, all of the overlaps can be detected by carrying out 1296 T3 polymerase reactions, 1296 T7 reactions and subsequent hybridization reactions. This is more efficient than the "fingerprinting" techniques generally used for genomic mapping by means of cosmid vectors.

Figure 4A:
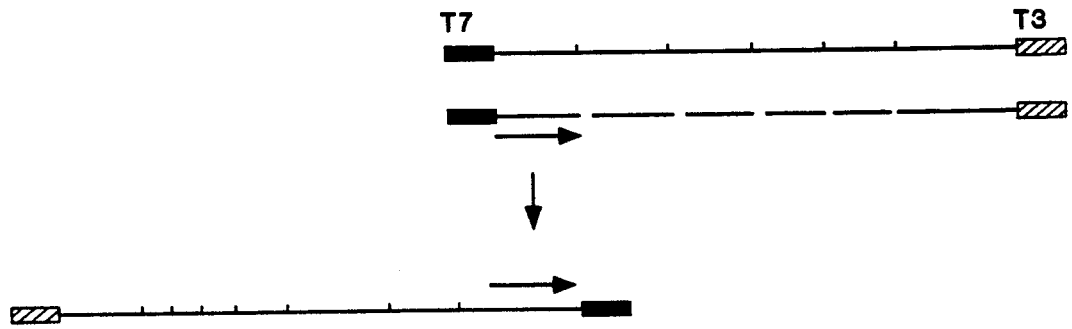
FIG. 4 illustrates the strategy for analysis of physical linkage using groups of cosmids.
Figure 4B:
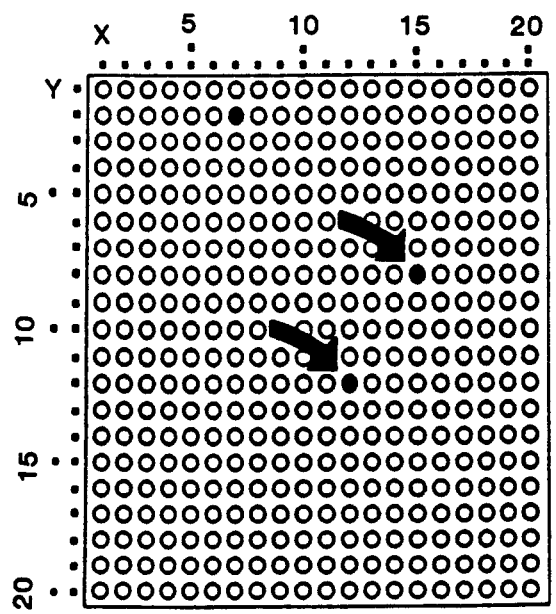
Figure 4D:
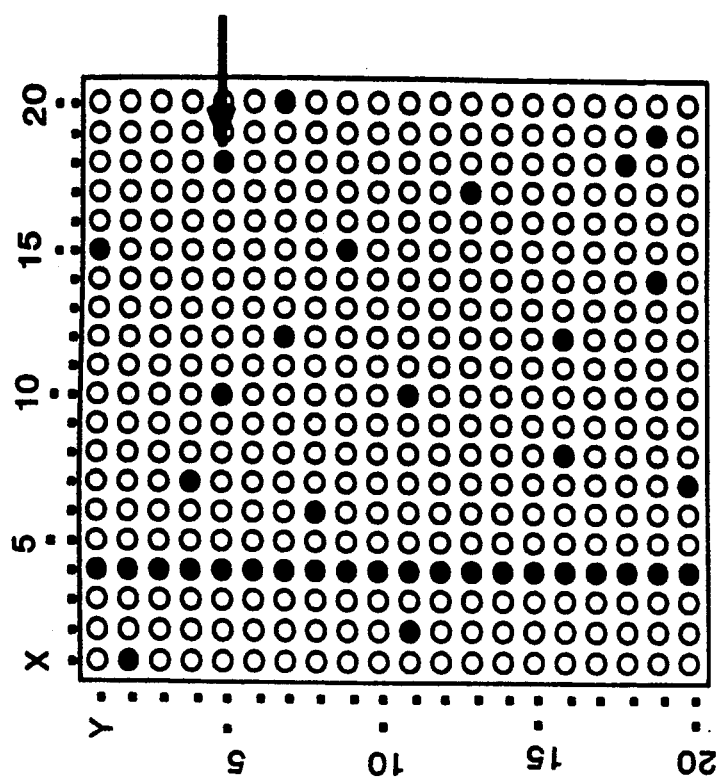
Figure 4C:
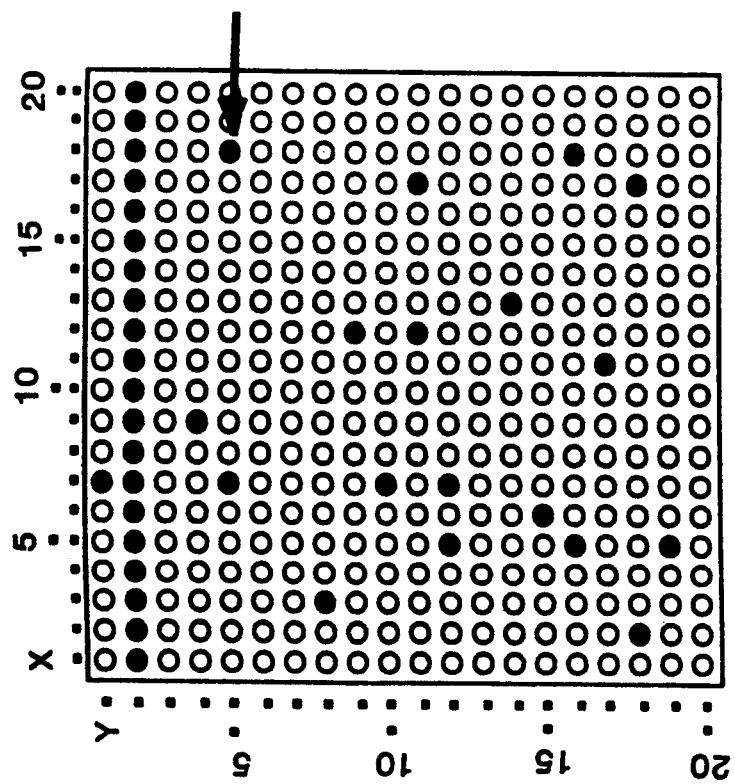

However, as an alternative to the individual analysis of cosmid clones for the detection of overlaps, the strategy of the present invention allows for the simultaneous analysis of multiple cosmid clones in groups. If all of the cosmid clones corresponding to a row of the matrix are pooled, DNA, RNA probes prepared from the pooled clones, prepared and hybridization carried out, a pattern of hybridizing clones is detected which includes all of the clones of the selected row, since each probe will hybridize to its own template, and a collection of clones representing all of clones overlapping with clones in the template groups (FIG. 4C). A similar procedure may be carried out using DNA prepared from pooled clones representing a column of the matrix, and a second set of cross-hybridizing clones is detected. Those clones which appear in both data sets will likely result from the same template clone being present in both groups of probes and a comparison of the two sets of data reveal the cross-hybridizing clones which are common to both data sets. The only template clone which is in common between the two sets of probes grouped together is that clone which is located at the intersection of the row and column of the matrix. If pooled probes are made from all of the grouped rows and columns, the analysis of all of the grouped probes will generate information on overlaps of all of the 1296 clones in the collection. By pooling 36 rows and 36 columns, all the linked clones can be detected carrying out merely 72 T3 polymerase reactions, 72 T7 polymerase reactions and subsequent hybridization reactions. Accordingly, this strategy allows the analysis of a collection of cosmid clones with far less effort than "fingerprinting" each of the clones selected individually.

The linked clones detected by the above method can then be grouped into contigs, either manually or, preferably, using appropriate computer programs. To confirm the correctness of the groupings, some of the contigs can be subjected to detailed restriction enzyme analysis, and the degree of physical overlap along with a physical map can be determined.

To complete a genomic map, the above-outlined procedure can be repeated with as many clones as necessary, and the gaps between the contigs can be filled in, e.g. by traditional chromosome walking.

The method described hereinabove represents a special case of a more general mapping strategy based on clone matrices of higher order. For instance, a similar type of mapping strategy can be carried out using a three dimensional matrix (n=3) rather than the two-dimensional matrix referred to above and illustrated in the examples. If 1000 cosmids were arranged in a 10×10×10 matrix and mixed RNA probes prepared from groups of 100 clones pooled according to the planes of the matrix, the clones hybridizing in common with three pooled probes would be linked to the clone at the intersection of the matrix in x, y, and z dimensions. Thus 1000 clones could potentially be linked using probes prepared with one RNA polymerase in 30 hybridization reactions. This strategy may be also extended to matrices of greater dimensionality.

TABLE 1

Theoretical analysis of genomes of various sizes by cosmid multiplex analysis where clones are organized in matrices of various dimensions and clones analyzed using probes prepared from groups of cosmid clones.

| dimension* $n$ | matrix size $d$ | probe pool size $d^{n-1}$ | number of clones analyzed $d^n$ | number of mixed probes $n \times d$ |
|---|---|---|---|---|
| 2 | 10 | 10 | 100 | 20 |
| 3 | 10 | 100 | 1000 | 30 |
| 2 | 36 | 36 | 1296 | 72 |
| 3 | 18 | 324 | 5832 | 54 |
| 3 | 36 | 1296 | 46,656 | 108 |
| 4 | 25 | 15,625 | 390,625 | 100 |

TABLE 1-continued

Theoretical analysis of genomes of various sizes by cosmid multiplex analysis where clones are organized in matrices of various dimensions and clones analyzed using probes prepared from groups of cosmid clones.

| dimension* $n$ | matrix size $d$ | probe pool size $d^{n-1}$ | number of clones analyzed $d^n$ | number of mixed probes $n \times d$ |
|---|---|---|---|---|
| 5 | 13 | 28,561 | 400,000 | 65 |

*Where a matrix of n dimensions containing $d^n$ cosmid is used for the arrangement of cosmid clones, pooled probes of $d^{n-1}$ members are prepared which allow for the analysis of $d^n$ individual clones by multiplex analysis using n × d mixed probes. For example, using a three dimensional matrix of 10 × 10 members, pooled probes of 100 individual clones could be used to analyze 1000 individual cosmids with 30 analytical reactions.

Given that the theoretical limit of detectable signal from pooled RNA probes is not reached, cosmids representing entire human genome with four-fold redundance can potentially be analyzed by the "multiplex" process of the present invention using a 5-dimensional matrix of n=13 in only 65 hybridization reactions. The theoretical limitation of this strategy seems to be the number of individual clones which can be pooled and still give reproducible hybridization signal and current protocols suggest that this limitation may be somewhat greater than 100 clones.

One major problem usually encountered with rapid chromosome "walking" using RNA probes prepared from cosmids is that repetitive sequences inadvertently present in the transcribed region near the end of the genomic insert may hybridize to many clones in a library, reducing the usefulness of the probe [Wahl et al., Supra, Cross et al., Gene 49, 9 (1986)]. To avoid this problem, the length of the RNA transcript has previously been limited to several hundred nucleotides by digesting the DNA with a frequently-cutting restriction enzyme before transcription. This decreases the probability that a repetitive sequence will occur in the probe, but has a number of disadvantages: 1) the signal strength of the probe may be severely decreased [Wahl et al., Supra]; 2) some probes may be by chance too small to be useful; 3) some end-specific RNA probes may still contain repetitive sequences if the sequence is at the immediate end of the clone. Also, it has been frequently noted that, in many RNA transcripts 1 to 5% of the probe consists of RNA sequences complementary to cosmid vector sequences. This material, which may be due to antegrade transcription of the T3 or T7 polymerase [Schenborn et al., Nucl. Acids Res. 13, 6223 (1985)] also tends to contribute to background hybridization when screening libraries.

To eliminate these problems, a prehybridization procedure has been developed using a mixture of DNA molecules containing human repetitive sequences. The RNA probe is annealed with the blocking mixture immediately after synthesis using a vast excess of repetitive sequences hybridized to high $C_o t$ value. Thus, any probe transcripts containing repetitive elements or complementary to the vector sequences will be effectively saturated. This blocking mixture contains DNA sequences complementary to most classes of human repetitive DNA, including Alu and minisatellite sequences, as well as plasmid sequences which suppress hybridization from low level vector RNA transcripts. This procedure is an important feature of the process according to the present invention.

Further details of the invention are illustrated by the following, non-limiting Example.

EXAMPLE

Analysis of Human Chromosome 11q

The cosmid vector sCOS-1 (FIG. 1) was used to prepare a genomic library from a somatic cell hybrid containing as its only human material DNA from the distal long arm of human chromosome 11, including 11q21-11qter, in a mouse background [Maslen et al., Genomics 2, 66 (1988)]. The distal long arm of human chromosome 11 is of biological interest for a number of reasons. Like the major histocompatibility complex, the T cell receptor and immunoglobulin genes, and the IgK-CD8A-CD8B region of chromosome 2p12, human chromosome 11q23 contains a cluster of genes encoding proteins which are members of the immunoglobulin superfamily and are possibly important for cell-cell interactions in the immune and nervous systems including Thy-1, CD3, δ, and epsilon, and N-CAM [Nguyen et al., J. Cell. Biol. 102, 711 (1986)]. 11q23 is the location of genes in which defects may be responsible for ataxia telangiectasia [Gatti et al., Nature 336, 577 (1988)] and other hereditary disorders including multiple endocrine neoplasia type I [Larsson et al., Nature 332, 85 (1988)], diabetes analogous to the NOD mouse [Prochazka et al., Science 237, 286 (1987)] and others are also likely linked to markers on leukemias and pathognomonic for Ewing's sarcoma, peripheral neuroepithelioma and Askin's tumor [Griffin et al., Proc. Natl. Acad. Sci. USA 83, 6122 (1986)]. The initial physical analysis of human chromosome 11 should allow eventual analysis of the genes associated with these phenomena and the underlying biology.

A genomic library consisting of $1.2 \times 10^7$ individual members was prepared and cosmids containing only human DNA were selected from this library by screening with probes recognizing human repetitive sequences. The proportion of human clones in this genomic library was 0.9%, indicating that the proportion of human chromosome 11 present in the somatic cell hybrid was about 27 mb, consistent with previous cytogenic and molecular characterization of this cell line [Maslen et al., Supra]. 1296 clones were selected, archived in 96-well microtitre plates, and arranged on a nitrocellulose filter according to the columns and rows of a 36×36 matrix. Using probes recognizing many available DNA markers mapping to this chromosome, cosmids containing the genes THY1 [van Rijs et al., Proc. Natl. Acad. Sci. USA 2, 5832 (1985)], T3D, T3E [Evans et al., Immunogen 28, 365 (1988)], ETS1 [Watson et al., Proc. Natl. Acad. Sci. USA 83, 1792 (1986)], PBG [Wang et al., Proc. Natl. Acad. Sci. USA 78, 5734 (1981)], PGR [Misrahi et al., Biochem. Biophys. Res. Commun. 143, 740 (1987)], SRPR [Lauffer et al., Nature 318, 334 (1985)], and APOA1 [Karathanasis et al., Proc. Natl. Acad. Sci. USA 80, 6147 (1983)]. The identified genes and clone coordinates for DNA markers on human chromosome 11q-11qter represented in the ordered cosmid set are shown in the following Table 2.

TABLE 2

Identified genes and clone coordinates for DNA markers on human chromosome 11q21-11qter represented in the ordered cosmid set.

| cosmid clone coordinate (Y, X) | marker |
|---|---|
| 3, 11 | THY1 |
| 11, 34 | THY1 |

TABLE 2-continued

Identified genes and clone coordinates for DNA markers on human chromosome 11q21-11qter represented in the ordered cosmid set.

| cosmid clone coordinate (Y, X) | marker |
|---|---|
| 10, 7 | T3D (CD3γ, δ) |
| 7, 13 | ETS1 |
| 5, 13 | ETS1 |
| 4, 22 | PGR |
| 13, 27 | APOA1 |
| 11, 25 | PBGD |
| 12, 19 | D11S23 |
| 24, 12 | D11S24 |
| 24, 8 | SRPR |
| 11, 31 | SRPR |

Additional available RFLP markers [Maslen et al., Supra] were also identified in this collection to allow eventual correlation of the emerging physical map of chromosome 11 with the linkage map.

Groups of clones corresponding to 32 of the rows and 36 columns were pooled, and 68 hybridization reactions were carried out to replica filters according to the strategy outlined hereinbefore. Mixed probes detected a minimum of nine and a maximum of 46 cross-hybridizing unique clones on the filter matrix with each hybridization reaction using a pooled probe [FIG. 5]. To aid in the analysis of the data generated by this procedure, the Y and X coordinates of the cross-hybridizing clones are entered into a computer and matches identified using one of several computer programs. From this series of experiments, 1099 linked clones were detected from the hybridization of 36 pooled columns and 32 pooled rows of the matrix. Several of these overlapping clones were analyzed by restriction mapping to confirm that the clones indeed did overlap in the expected manner.

Completeness of the Cosmid Multiplex Data

From the list of linked clones produced by this multiplex technique, contigs were assembled either manually or through computer analysis of the data from the predicted hybridization linkage using mixed multiple RNA probes. Based on an initial analysis of the data using a simple algorithm for contig construction, 315 contigs were assembled from the 1099 linked clones determined from multiplex analysis. The size of the contigs ranged from 2 linked cosmids to 27 cosmids grouped into a contig extending over several hundred kb, with the majority of contigs consisting of between 2 and 5 cosmids. To confirm that these groupings reflected the true structure of the human chromosome, and not artifactual groupings due to random cross-hybridization, several of the contigs were restriction mapped in detail to determine the degree of overlap and establish a physical map. The restriction map of a representative contig assembled by this strategy is shown in FIG. 6.

Assessment of Progress

Based on the assumption that the region of human chromosome 11 carried by the parent hybrid represents about 27 mb, the collection of 1296 cosmid clones analyzed here represents about 2 genome equivalents. It is also estimated that the minimal detectable overlap by hybridization analysis using end-specific RNA probes is about 200 nucleotides. If $\Theta$ is the fraction of length of two clones which must be shared in order for overlap to be detected [Lander et al., Supra], then the expected number of contigs consisting of at least two clones generated by the analysis of N cosmid clones is $$Ne^{-c(1-\Theta)} - Ne^{-2c(1-\Theta)}$$

wherein the redundancy of coverage, $c = LN/G$, where L is the length of the clone insert and G is the haploid genome length in bp.

In contrast to fingerprinting methods, where may range from 0.15 to 0.5, the minimum detectable overlap with end-specific RNA probes is $\Theta = 0.005$, approaching the theoretical limit of $\Theta = 0$, a maximum of about 450 contigs would be expected to result after the analysis of one genome equivalent and about 260 contigs after the analysis of 2 genome equivalents [Lander et al., Supra]. Thus the analysis of the clone set carried out here, generating 315 contigs after the analysis of about two genome equivalents, is in good agreement with theoretical predictions. The main advantage of the current strategy is that the analysis of 1296 clones required only 72 analytical reactions, rather than 1296.

It was found that the prehybridization of the RNA probes with a high concentration of human repetitive sequences, as hereinabove described, was sufficient to completely block hybridization of most of these frequencies, and was sufficient for eliminating most of these artifactual linkages. However, the analysis of several large contigs mapping to human chromosome 11 generated by this analysis has revealed several cosmid clones which were included in a contig but which could not be substantiated based on the result of restriction mapping and hybridization analysis. This artifact may be the result of cryptic low-frequency repetitive or redundant sequences present in this region of the genome, or could be the result of genomic sequences which are unstable and deleted or rearrange when cloned in E. coli. Evidence for the later sequences, isolated through screening non-amplified cosmid libraries, has been found in the analysis of the human CD3 locus [Evans et al., Immunogen, Supra]. However, it should be noted that the multiplex technique of the present invention, when carried to completion using both T3 and T7 mixed RNA probes, generates data that is internally redundant in that both members of a linked pair should cross-hybridize with one another. Thus, further refinement of this approach should eliminate most serious artifacts arising during multiplex clone analysis.

In this regard, the analysis disclosed in the present invention has generated a partially overlapping cosmid set which is estimated to include about 60% of the 11q21-11qter region of human chromosome 11q. The results of certain preliminary restriction enzyme analyses, further analysis of contigs and filling-in by traditional chromosome walking are in complete agreement with theoretical calculations of fingerprinting efficiency. A more complete analysis of this and other chromosome regions using a number of cosmids for 4 or more genome equivalents would be expected to result in near closure of the map. Using the technique of the present invention, this would require a collection of about 3600 cosmids and 120 T3 or T7 reactions/hybridizations rather than the 72 carried out in the present Example. In addition, the technique of the present invention is applicable for traditional chromosome "walking" to allow "filling-in" of gaps in a near complete map.

Additional analysis of this cosmid set representing chromosome 11q can be completed by automated restriction mapping. Analysis to date has revealed the presence of 177 potential "linking" clones, containing one or more NotI restriction sites, and 77 clones containing Sac2 sites indicative of hypomethylated CpG-rich islands. 40 of these cosmid clones contain clustered rare CpG rich restriction sites and can be identified unequivocally as hypomethylated islands. In addition, cosmid clones have recently proved very useful for in situ hybridization to metaphase or interphase chromosomes [Lichter et al., *Proc. Natl. Acad. Sci. USA* 85, 9664 (1988)] and the identification of the cytogenic location of single-copy DNA sequences. These procedures potentially will allow ordering cosmid contigs with resolution of greater than 500 kb and, coupled with the strategy described here, provide a powerful mechanism for the constructions of physical maps of chromosomes.

I claim:

1. A method for simultaneous identification of overlapping cosmid clones among multiple cosmid clones, comprising:
   (a) arranging the multiple cosmid clones, whereby each clone may be identified and replicas of said arrangement may be generated;
   (b) pooling a first portion of the multiple cosmid clones and synthesizing mixed end-specific RNA probes from the DNA inserts that have been prepared from said pooled clones, wherein said portion includes less than all of said multiple cosmid clones;
   (c) hybridizing the probes to a replica of said arranged cosmid clones and identifying the cosmid clones in the replica that hybridize to the probes, wherein said identified clones include the pooled cosmid clones and cosmid clones that contain DNA inserts that overlap with the DNA inserts in the pooled clones;
   (d) repeating said hybridization step with a second portion of mixed end-specific probes that are prepared from a second pooled portion of multiple cosmid clones; and
   (e) identifying the cosmid clones in each replica to which both the probes of steps b) and d) hybridize thereby identifying overlapping clones.

2. The method of claim 1, wherein said second portion includes at least one clone that was present in the first portion.

3. The method of claim 1, wherein one clone from said first portion is added to said second portion of pooled clones prior to preparing probes therefrom, whereby the clones that hybridize to both portions of probes, other than those that include the DNA inserts from which the probes were synthesized, contain DNA inserts that overlap with said added clone from the first portion.

4. The method of claim 1, further comprising:
   (f) repeating said hybridization step with an additional portion of mixed end-specific probes that are prepared from an additional portion of the pooled multiple clones, wherein said additional portion includes at least one clone that was present in the first and second portions, but does not include any other clones that were previously pooled; and
   (g) identifying the cosmid clones in the library to which the probes of steps b), e), and f) hybridize, wherein the identified clones are other than those which correspond to the pooled clones.

5. The method of claim 4, further comprising:
   (h) repeating steps (f) and (g) a plurality of times until all of the cosmid clones in the library have been pooled and hybridized to the library.

6. The method of claim 1, wherein the arrangement is a two-dimensional matrix and the clones are pooled pairwise according to the rows and columns of a two-dimensional matrix.

7. The method of claim 1, wherein the arrangement is a three-dimensional matrix and the clones are pooled according to intersecting planes of the three-dimensional matrix, wherein following hybridization the replicas are compared according to intersecting planes of the matrix.

8. The method of claim 7, wherein groups of three replicas produced by hybridizing probes prepared from pooled clones according to three intersecting planes are compared, whereby the clones on all three replicas that hybridize to probes from each of the pooled clones include DNA that overlaps with the clone that occurs at the intersection of the three planes.

9. The method of claim 1, wherein said cosmid clones include sequence of nucleotides flanking at least one end of the inserted DNA that serve as promoters for the synthesis of the end-specific probes.

10. The method of claim 9, wherein said at least one of the flanking sequences includes a sequence of nucleotides that is recognized as a promoter by a bacteriophage polymerase, and that is positioned operatively for transcription of the inserted DNA fragment.

11. The method of claim 10, wherein both flanking sequences include sequences of nucleotides that are recognized as promoters by a bacteriophage RNA polymerase, wherein said promoters are oppositely oriented and positioned operatively for transcription of the inserted DNA fragment.

12. The method of claim 11, wherein each of the bacteriophage RNA polymerase-specific promoters is selected from the group consisting of promoters specific for bacteriophage T7 RNA polymerase, and promoters specific for bacteriophage T3 RNA polymerase.

13. The method of claim 9, wherein said cosmid clones are prepared by inserting DNA fragments into the cloning sites of a cosmid vector selected from the group consisting of pWE8, pWE10, pWE15, and pWE16.

14. The method of any one of claims 10 through 12, wherein said cosmid clones include at least two cos sites.

15. The method of claim 9, wherein said cosmid clones are prepared by inserting DNA fragments into the cloning sites of a cosmid vector selected from the group consisting of sCOS-1, sCOS-2, and sCOS-4.

16. A method for physical mapping of complex genomes comprising:
   (a) preparing a genomic library of cosmid clones by inserting DNA fragments from said genome into cosmid vectors, wherein the cosmid vectors include sequences of nucleotides that flank at least one end of the inserted DNA and that serve as transcription initiation sites for the synthesis of end-specific probes;
   (b) arranging the cosmid clones, whereby each clone may be identified and replicas of said arrangement may be generated;
   (c) pooling portions of cosmid clones and synthesizing pools of mixed end-specific probes from the DNA inserts that have been prepared from said pooled clones, wherein each pool contains fewer than all of the cosmid clones in the library but all of the cosmid clones in the library are included in at least one pool;

(d) hybridizing each pool of probes to a replica of said arranged cosmid clones and identifying the cosmid clones in each replica that hybridize to the probes, wherein said identified clones include the pooled cosmid clones and cosmid clones that contain DNA inserts that overlap with the DNA inserts in the pooled clones;

(e) identifying the cosmid clones from among those identified in step (d) the clones that hybridize to two or more pools of probes, thereby identifying groups of cosmid clones that include overlapping DNA; and (g) assembling contigs from said groups into a physical map of the genome from which the library was derived.

17. The method of claim 16, wherein each portion includes at least one common clone that was present in one of the other portions, whereby the clones identified in step (e) contain DNA inserts that overlap with the common clone.

18. The method of claim 16, wherein in step (e) the cosmid clones in each replica that include clones that hybridize to two or more pools are identified by comparing pairs of replicas produced by hybridizing pools that include one clone in common.

19. The method of claim 16, wherein the location of each individual clone in the replica is identified by unique coordinates that describe the location of the clone in the replica.

20. The method of claim 16, wherein the arrangement is a matrix, and the location of each clone int he matrix is uniquely identified by at least two coordinates.

21. The method of claim 20, wherein the clones whose locations include one or more common coordinates and at least one different coordinate are pooled in step (c).

22. The method of claim 16, wherein said cosmid vectors contain at least one promoter specific for a bacteriophage RNA polymerase and a cloning site for the insertion of DNA fragments, wherein aid promoter is positioned operatively for transcription of a DNA fragment into said cloning site.

23. The method of claim 22, wherein said cosmid vectors contain two oppositely oriented promoters, each of which is specific for a bacteriophage RNA polymerase and is positioned operatively for transcription of a DNA fragment inserted into said cloning site.

24. The method of claim 23, wherein each of said bacteriophage RNA polymerase-specific promoters is selected from the group consisting of promoters specific for bacteriophage T7 RNA polymerase, and promoters specific for bacteriophage T3 RNA polymerase.

25. The method of claim 24, wherein said cosmid vector is selected from the group consisting of pWE8, pWE10, pWE15, and pWE16.

26. The method of any one of claims 17 through 20, wherein said cosmid vectors contain at least two cos sites.

27. The method of claim 26, wherein said cos sites are separated by unique restriction sites.

28. The method of claim 27, wherein said cosmid vector is selected from the group consisting of sCOS-1, sCOS-2, and sCOS-4.

* * * * *

UNITED STATES PATENT AND TRADEMARK OFFICE
CERTIFICATE OF CORRECTION

PATENT NO. : 5,219,726
DATED : June 15, 1993
INVENTOR(S) : Evans, Glen A.

It is certified that error appears in the above-indentified patent and that said Letters Patent is hereby corrected as shown below:

Column 1, line 55, after "(1987)]" insert --.--.
Column 2, line 64, "Methods in Enzymology" should be --*Methods in Enzymology*--.
Column 7, line 62, "recA." should be --reA--.
Column 13, line 19, before "Estivill" insert --[--.
Column 15, lines 18-19, "redundance" should be --redundancy--.
Column 8, line 7, after "No." insert --37503--.
Column 8, line 9, "U.S.A. 37503" should be --U.S.A.--.
Column 10, line 13, after "as" insert --described--.
Column 10, line 15, "181,836 described" should be --181,836--.
Column 22, line 2, "int he" should be --in the--.
Column 22, line 11, "aid" should be --said--.
Column 22, line 27, "17 through 20" should be --any of claims 21, 22, 24 or 25--.

Signed and Sealed this

Twenty-first Day of March, 1995

Attest:

BRUCE LEHMAN

Attesting Officer     *Commissioner of Patents and Trademarks*